United States Patent
Hitzel et al.

[11] 3,950,524
[45] Apr. 13, 1976

[54] HYPOGLYCEMIC BENZENESULFONAMIDO PYRIMIDINES

[75] Inventors: Volker Hitzel, Lorsbach, Taunus; Rudi Weyer, Frankfurt am Main; Walter Aumuller, Kelkheim, Taunus, all of Germany

[73] Assignee: Hoechst Aktiengesellschaft, Frankfurt am Main, Germany

[22] Filed: Jan. 14, 1975

[21] Appl. No.: 540,964

[30] Foreign Application Priority Data
Jan. 16, 1974 Germany............................ 2401879

[52] U.S. Cl............................ 424/251; 260/256.5 R
[51] Int. Cl.² ............... A61K 31/505; C07D 239/00
[58] Field of Search............... 260/256.5 R; 424/251

[56] References Cited
UNITED STATES PATENTS
3,621,026  11/1971  Gutsche et al............... 260/256.5 R
3,816,424  6/1974  Weyer et al................. 260/256.5 R Primary Examiner—Leonard Schenkman
Attorney, Agent, or Firm—Curtis, Morris & Safford

[57] ABSTRACT

Sulfonamidopyrimidines of the formula

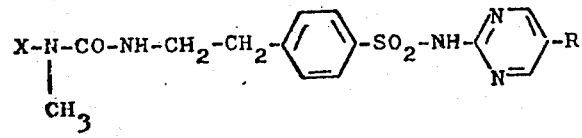

in which X is a 6-membered heteroaromatic ring including 1 to 2 nitrogen atoms which may be substituted with 1 or 2 methyl groups and/or fused with benzene and is linked in vicinal position with regard to the nitrogen atom to the rest of the molecule, R is alkyl or alkoxy, having 1 to 4 carbon atoms each, their manufacture and their use as hypoglycemic agents.

6 Claims, No Drawings

HYPOGLYCEMIC BENZENESULFONAMIDO PYRIMIDINES

The present invention relates to sulfonamido-pyrimidines of the formula

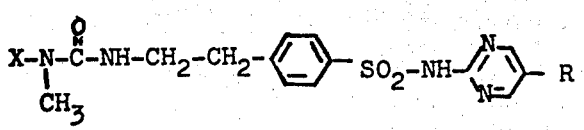

in which X is a 6-membered heteroaromatic ring including 1 to 2 nitrogen atoms, which may be substituted with 1 or 2 methyl groups and/or fused with a benzene nucleus and is linked in vicinal position with regard to the nitrogen atom to the rest of the molecule, R is alkyl or alkoxy, having 1 to 4 carbon atoms each.

The compounds of the invention have, as such or in the form of their salts, hypoglycemic properties and are distinguished by a strong and long-lasting lowering effect on the blood sugar level.

This invention further relates to a process for the manufacture of these benzene-sulfonamido-pyrimidines, which comprises a. reacting a compound of the formula

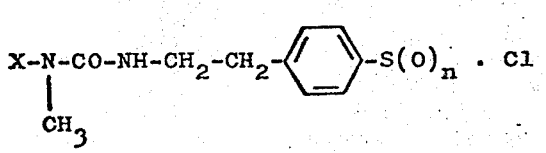

in which X is defined as above and $n$ is zero or the integer 1 or 2, with a 2-amino-pyrimidine of the formula

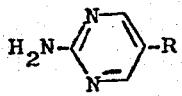

in which R is defined as above, and optionally oxidizing the compound thus obtained to yield a sulfonamide, or b. reacting a benzene-sulfonyl-guanidine of the formula

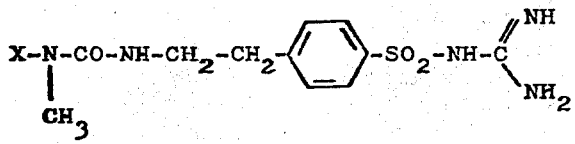

in which X is defined as above, with a compound of the formula

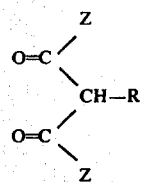

in which R is defined as above, and Z and Z' each stands for hydrogen or an alkoxy group, or the functional derivative thereof, and then converting the pyrimidine, which may be hydroxylated in 4- and/or 6-position, by conversion into the halogenated compound and subsequent reductive dehalogenation into the desired pyrimidine, or c. reacting a benzene-sulfonamide of the formula

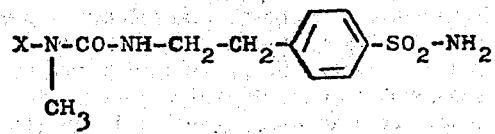

in which X is defined as above, with a pyrimidine derivative of the formula

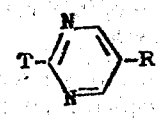

in which R is defined as above, and T stands for a reactive ester group, the group $-NH.NO_2$, $-NHCN$ or a lower trialkyl ammonium group, or d. reacting a compound of the formula

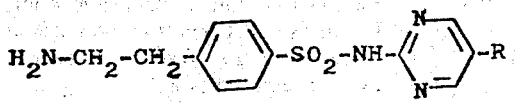

in which R is defined as above, with a reactive derivative of an acid of the formula

in which X is defined as above, and optionally converting the reaction product into a physiologically acceptable salt.

The reaction of the components mentioned sub (a) is advantageously carried out in an inert solvent in the presence of a preferably organic base, such as pyridine or trimethylamine. It may, however, also be carried out using a molar excess amount of amino-pyrimidine to bind the hydrogen chloride formed during the reaction. The subsequent oxidation reaction of the sulfenyl amides ($n = 0$) or sulfinyl amides ($n = 1$) is carried out in the usual manner, for example by treating them with hydrogen peroxide, potassium permanganate or nitric acid.

The sulfochlorides used as starting compounds for method (a) are prepared, for example by reacting carbamic acid chloride of the formula

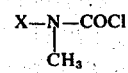

which has been prepared from the methylamino compound of the heterocycle X and phosgene, with phenyl-ethyl amine and by converting the urea obtained with chlorosulfonic acid into an ureido-ethyl-benzenesulfochloride substituted by the heteroaromatic ring X and the methyl group.

This sulfonyl chloride can be reduced in known manner to sulfinic or sulfenic acid, from which the corresponding chloride can then be prepared.

The acylamino-alkyl-benzenesulfonyl-guanidines can be condensed with the β-dicarbonyl compounds according to method (b) using, for example an alkali metal alcoholate in an alcohol. For this purpose, the β-dicarbonyl compounds are used in the free form or as the functional derivatives, for example acetals; they may also be prepared in a single-step process according to Vilsmeier from aldehyde acetals or the corresponding enamines, an inorganic acid chloride and dialkyl formamide. When, instead of the dicarbonyl compounds, corresponding by substituted malonic acid diesters, malonic ester aldehydes or the functional derivatives thereof are used, the hydroxyl groups linked in 4- and/or 6-position to the pyrimidine ring have then to be substituted by means of an inorganic acid chloride with chlorine atoms which can then easily be exchanged against hydrogen atoms by reduction, for example with zinc powder.

The acylaminoalkyl-benzene-sulfonyl-guanidines used as starting compounds can be obtained, for example by fusing the acylaminoalkyl-benzenesulfonamides with guanidine carbonate. Ureido-ethylbenzene-sulfochloride may also be reacted with guanidine to yield the sulfonyl guanidine.

The condensation reaction of benzenesulfonamides with the pyridine derivatives according to method (c) is preferably carried out in the presence of a basic compound, such as potassium carbonate.

As starting compounds suitable for the reaction according to method (c), 2-halogeno-pyrimidines obtained by reacting 2-hydroxypyrimidines with excess phosphoroxy chloride are especially useful. Instead of 2-halogeno-pyrimidines, the corresponding trialkylammonium-pyrimidines, nitroamino-pyrimidines or cyanoamino-pyrimidines may also be reacted.

The aminoalkyl-benzenesulfonamido-pyrimidines are acylated with the X-substituted acids according to method (d) in the usual manner by reacting a reactive carbamic acid derivative with an amino compounds, suitably in the presence of an acidbinding agent.

The hypoglycemic activity of the said benzenesulfonamidopyrimidines can be established by administering them to normally fed rabbits in the form of the free compounds or of their sodium salts in a dosage unit of 10 mg/kg of body weight, and then determining the blood sugar values over a prolonged period of time according to the method of Hagedorn-Jensen or by means of an autoanalyzer.

The following Table comprises the hypoglycemic actions of some compounds obtained according to the invention, namely
4-(β-N'-methyl-N'-2-pyridylureido-ethyl)-N-(5-isobutyl-2-pyrimidinyl)-benzenesulfonamide (compound I),
4-(β-N'-2-quinolyl-N'-methylureido-ethyl)-N-(5-ethyl-2-pyrimidinyl)-benzenesulfonamide (compound II) and
4-(β-N'-[4,6-dimethyl-2-pyrimidinyl]-N'-methylureido-ethyl)-N-(5-ethyl-2-pyrimidinyl)-benzenesulfonamide (compound III).

TABLE

Blood sugar lowering rate in percent, upon oral administration of 10 mg/kg each of compounds I to III after ....... hours

| Compound | 1 | 3 | 6 | 24 | 48 hours |
|---|---|---|---|---|---|
| I | −18 | −28 | −25 | −23 | 0 |
| II | 0 | −18 | −30 | −34 | 0 |
| III | −28 | −25 | −40 | −22 | 0 |

The said benzene-sulfonamido-pyrimidines are preferably used for the manufacture of orally administerable preparations having hypoglycemic activity in the treatment of diabetes mellitus and may be administered as such or in the form of their salts or in the presence of substances causing salt formation. For the salt formation, for example alkaline agents may be used, such as alkali metal or alkaline earth metal hydroxides, carbonates or bicarbonates.

As pharmaceutical compositions, there are preferably mentioned tablets which contain, in addition to the products of the invention as active ingredients, the usual carrier and excipients, such as talcum, starch, lactose, tragacanth or magnesium stearate.

A preparation containing the said benzene-sulfonamido-pyrimidine as the active ingredient, for example a tablet or a powder, with or without an additive, is advantagously brought into a pharmaceutically suitable dosage unit form, so as to comply with the activity of the benzene-sulfonamido-pyrimidine used and with the desired effect. An appropriate dosage unit ranges from about 1 to 100 mg, preferably from 5 to 50 mg/kg of body weight, but higher or lower dosage units are also suitable, which may be divided or multiplied prior to administration.

The new compounds may also be combined with other active substances, especially with other antidiabetics, such as biguanides, for example phenformin, buformin and metformin; geriatrics or vitamins.

The following Examples illustrate the invention.

EXAMPLE 1

4-(β-N'-methyl-N'-2-pyridyl-ureidoethyl)-N-(5-isobutyl-2-pyrimidinyl)-benzenesulfonamide 1.7 Grams of N-methyl-N-2-pyridyl-carbamic acid chloride (prepared from 2-methylamino-pyridine and phosgene in benzene with pyridine as an acid-binding agent) were dissolved in 10 ml of acetone and the solution was added dropwise while cooling with ice to a solution of 4-(β-aminoethyl)-N-(5-isobutyl-2-pyrimidinyl)-benzenesulfonamide. This latter solution had been obtained by saponifying 4.05 g of 4-(β-ethoxycarboxamido-ethyl)-N-(5-isobutyl-2-pyrimidinyl)-benzenesulfonamide (m.p. 151° − 152°C) with a 10% sodium hydroxide solution and by adding water, glacial acetic acid and acetone thereto. The mixture was heated to room temperature and stirring was continued for 1 hour. After dilution with water and filtration, the mixture was acidified with dilute acetic acid, suction-filtered, and 4-(β-N'-methyl-N'-2-pyridyl-ureidoethyl)-N-(5-isobutyl-2-pyrimidinyl)-benzenesulfonamide was recrystallized from methanol/water. The substance melted at 177° − 179°C.

In an analogous manner, there was obtained 4-(β-N'-2-quinolyl-N'-methylureidoethyl)-N-(5-isobutyl-2-pyrimidinyl)-benzenesulfonamide, m.p. 151° − 153°C (from methanol), from 4-(β-ethoxycarboxamido-ethyl)-N-(5-isobutyl-2-pyrimidinyl)-benzenesulfonamide by reaction with N-2-quinolyl-N-methyl-carbamic acid chloride (prepared from 2-methylamino-quinoline and phosgene.

In an analogous manner, the reaction of 4-(β-ethoxycarboxamidoethyl)-N-(5-isobutoxy-2-pyrimidinyl)-benzenesulfonamide, m.p. 158°C, with N-methyl-N-2-pyridyl-carbamic acid chloride yielded 4-(β-N'-methyl-N'-2-pyridylureido-ethyl)-N-(5-isobutoxy-2-pyrimidinyl)-benzene-sulfonamide, m.p. 149° – 151°C (from methanol) and the reaction with N-2-quinolyl-N-methyl-carbamic acid chloride yielded 4-(β-N'-2-quinolyl-N'-methylureidoethyl)-N-(5-isobutoxy-2-pyrimidinyl)-benzenesulfonamide, m.p. 151° – 153°C (from methanol).

In an analogous manner, the reaction of 4-(β-ethoxycarboxamidoethyl)-N-(5-propyl-2-pyrimidinyl)-benzene-sulfonamide, m.p. 162° – 163°C, with N-methyl-N-2-pyridyl-carbamic acid chloride yielded 4-(β-N'-methyl-N'-2-pyridylureidoethyl)-N-(5-propyl-2-pyrimidinyl)-benzene-sulfonamide, m.p. 169° – 171°C (from methanol/water) and the reaction with N-2-quinolyl-N-methyl-carbamic acid chloride yielded 4-(β-N'-2-quinolyl-N'-methylureidoethyl)-N-(5-propyl-2-pyrimidinyl)-benzenesulfonamide, m.p. 170° – 172°C (from methanol/dioxan).

In an analogous manner, the reaction of 4-(β-ethoxycarboxamidoethyl)-N-(5-ethyl-2-pyrimidinyl)-benzenesulfonamide, m.p. 163° – 165°C, with N-methyl-N-2-pyridyl-carbamic acid chloride yielded 4-(β-N'-methyl-N'-2-pyridylureidoethyl)-N-(5-ethyl-2-pyrimidinyl)-benzenesulfonamide, m.p. 188° – 190°C (from methanol), the reaction with N-2-quinolyl-N-methyl-carbamic acid chloride yielded 4-(β-N'-quinolyl-N'-methylureidoethyl)-N-(5-ethyl-2-pyrimidinyl)-benzene-sulfonamide, m.p. 194° – 196°C (from methanol/dioxan); the reaction with N-(4,6-dimethyl-2-pyrimidinyl)-N-methyl-carbamic acid chloride (prepared from 4,6-dimethyl-2-methyl-amino-pyrimidine and phosgene) yielded the 4-(β-N'-[4,6-dimethyl-2-pyrimidinyl]-N'-methylureidoethyl)-N-(5-ethyl-2-pyrimidinyl)-benzene-sulfonamide, m.p. 196° – 198°C (from methanol/dioxan).

In an analogous manner, the reaction of 4-(β-ethoxycarboxamidoethyl)-N-(5-butyl-2-pyrimidinyl)-benzene-sulfonamide, m.p. 114° – 116°C, with N-methyl-N-2-pyridyl-carbamic acid chloride yielded 4-(β-N'-methyl-N'-2-pyridylureidoethyl)-N-(5-butyl-2-pyrimidinyl)-benzene-sulfonamide, m.p. 174° – 176°C (from methanol).

We claim:

1. A sulfonamido pyrimidine of the formula

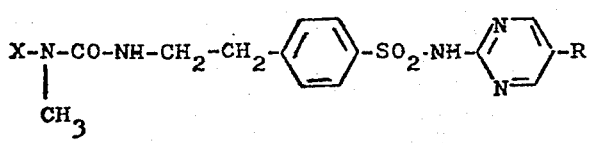

in which X is a 6-membered heterocyclic ring containing 1 or 2 nitrogen atoms which may be substituted with 1 or 2 methyl groups; or quinolyl, and is linked to the rest of the molecule at the 2-position of said heterocyclic ring, and R is alkyl or alkoxy having 1 to 4 carbon atoms, or a pharmaceutically acceptable salt thereof.

2. A sulfonamido pyrimidine of the formula

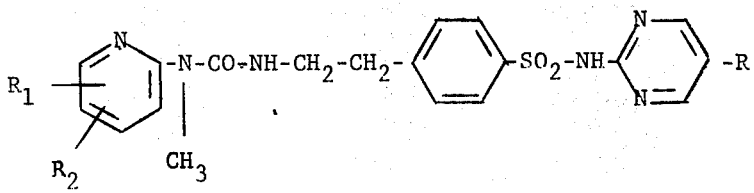

in which R is alkyl or alkoxy of 1 to 4 carbon atoms and $R_1$ and $R_2$ are H or methyl.

3. The compound of claim 2 which is 4-(β-N'-methyl-N'-2-pyridylureidoethyl)-N-(5-isobutyl-2-pyrimidinyl)-benzenesulfonamide.

4. The compound of claim 2 which is 4-(β-N'-methyl-N'-2-pyridylureidoethyl)-N-(5-propyl-2-pyrimidinyl)-benzenesulfonamide.

5. A pharmaceutical composition for lowering blood sugar level which comprises an effective amount of a sulfonamido pyrimidine of claim 1 and a carrier therefore.

6. A method of lowering the blood sugar level in a patient in need thereof which comprises administering an effective amount of a sulfonamido pyrimidine of claim 1 to said patient.

* * * * *